United States Patent
Thakur et al.

(10) Patent No.: US 11,406,283 B2
(45) Date of Patent: Aug. 9, 2022

(54) HFPEF DETECTION USING EXERTIONAL HEART SOUNDS

(71) Applicant: Cardiac Pacemakers, Inc., St. Paul, MN (US)

(72) Inventors: Pramodsingh Hirasingh Thakur, Woodbury, MN (US); Bin Mi, Arden Hills, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 216 days.

(21) Appl. No.: 16/709,382

(22) Filed: Dec. 10, 2019

(65) Prior Publication Data
US 2020/0178850 A1 Jun. 11, 2020

Related U.S. Application Data (60) Provisional application No. 62/777,977, filed on Dec. 11, 2018.

(51) Int. Cl.
*A61B 5/00* (2006.01)
*A61B 5/11* (2006.01)

(52) U.S. Cl.
CPC .......... *A61B 5/1102* (2013.01); *A61B 5/1116* (2013.01); *A61B 5/1118* (2013.01); *A61B 5/7275* (2013.01); *A61B 2562/0219* (2013.01)

(58) Field of Classification Search
CPC ... A61B 5/1102; A61B 5/1116; A61B 5/1118; A61B 5/7275; A61B 2562/0219; A61B 7/00
See application file for complete search history.

(56) References Cited

U.S. PATENT DOCUMENTS

| | | | |
|---|---|---|---|
| 7,115,096 B2 | 10/2006 | Siejko et al. | |
| 7,972,275 B2 | 7/2011 | Siejko et al. | |
| 8,048,001 B2 | 11/2011 | Patangay et al. | |
| 9,345,410 B2 | 5/2016 | Thakur et al. | |
| 9,433,792 B2 | 9/2016 | Rosenberg et al. | |
| 9,622,664 B2 | 4/2017 | An et al. | |

(Continued)

FOREIGN PATENT DOCUMENTS

| CN | 113453625 A | 9/2021 |
|---|---|---|
| WO | WO-2018189671 A1 | 10/2018 |

(Continued)

OTHER PUBLICATIONS

"U.S. Appl. No. 16/845,730, Examiner Interview Summary dated Dec. 13, 2021", 2 pgs.

(Continued)

*Primary Examiner* — Rex R Holmes
*Assistant Examiner* — Sana Sahand
(74) *Attorney, Agent, or Firm* — Schwegman Lundberg & Woessner, P.A.

(57) ABSTRACT

This document discusses, among other things, systems and methods to determine an indication of heart failure with preserved ejection fraction (HFpEF) of a subject using a determined change in cardiac acceleration information of the subject at exertion relative to cardiac acceleration information of the subject at rest. The system can include a signal receiver circuit configured to receive cardiac acceleration information of a subject and exertion information of the subject, and an assessment circuit configured to determine the change in cardiac acceleration information of the subject at exertion relative to cardiac acceleration information of the subject at rest, and to determine an indication of HFpEF of the subject using the determined change in cardiac acceleration information.

20 Claims, 5 Drawing Sheets

(56) References Cited

U.S. PATENT DOCUMENTS

| | | | |
|---|---|---|---|
| 9,968,266 | B2 | 5/2018 | An et al. |
| 2003/0204145 | A1 | 10/2003 | Manolas |
| 2004/0106960 | A1 | 6/2004 | Siejko et al. |
| 2006/0282000 | A1* | 12/2006 | Zhang ............... A61B 5/024 600/528 |
| 2009/0287106 | A1 | 11/2009 | Zhang et al. |
| 2012/0157797 | A1 | 6/2012 | Zhang et al. |
| 2014/0276163 | A1* | 9/2014 | Thakur ............... A61B 5/7275 600/528 |
| 2016/0220357 | A1 | 8/2016 | Anand et al. |
| 2017/0239472 | A1 | 8/2017 | Zhang et al. |
| 2019/0298903 | A1 | 10/2019 | Gillberg et al. |
| 2020/0324120 | A1 | 10/2020 | Yu et al. |
| 2020/0324121 | A1 | 10/2020 | Yu et al. |

FOREIGN PATENT DOCUMENTS

| | | |
|---|---|---|
| WO | WO-2019144058 A1 | 7/2019 |
| WO | WO-2020123487 A1 | 6/2020 |

OTHER PUBLICATIONS

"U.S. Appl. No. 16/845,730, Non Final Office Action dated Sep. 1, 2021", 11 pgs.

"U.S. Appl. No. 16/845,730, Response filed Dec. 1, 2021 to Non Final Office Action dated Sep. 1, 2021", 12 pgs.

"U.S. Appl. No. 16/845,762, Examiner Interview Summary dated Dec. 13, 2021", 2 pgs.

"U.S. Appl. No. 16/845,762, Non Final Office Action dated Sep. 1, 2021", 11 pgs.

"U.S. Appl. No. 16/845,762, Response filed Dec. 1, 2021 to Non Final Office Action dated Sep. 1, 2021", 11 pgs.

"International Application Serial No. PCT/US2019/065455, International Preliminary Report on Patentability dated Jun. 24, 2021", 9 pgs.

"International Application Serial No. PCT/US2019/065455, International Search Report dated Apr. 2, 2020", 6 pgs.

"International Application Serial No. PCT/US2019/065455, Written Opinion dated Apr. 2, 2020", 7 pgs.

* cited by examiner

HFPEF DETECTION USING EXERTIONAL HEART SOUNDS

CLAIM OF PRIORITY

This application claims the benefit of priority under 35 U.S.C. § 119(e) of U.S. Provisional Patent Application Ser. No. 62/777,977, filed on Dec. 11, 2018, which is herein incorporated by reference in its entirety.

TECHNICAL FIELD

This document relates generally to medical devices, and more particularly, but not by way of limitation, to systems, devices, and methods for monitoring or detecting heart failure with preserved ejection fraction (HFpEF) using exertional heart sounds.

BACKGROUND

Heart failure (HF) is a reduction in the ability of the heart to deliver enough blood to meet bodily needs, affecting over five million patients in the United States alone. HF patients commonly have enlarged heart with weakened cardiac muscles, resulting in reduced contractility and poor cardiac output of blood. Typical signs of HF include: pulmonary congestion; edema; difficulty breathing; etc.

Ejection fraction (EF) is a measure of pumping efficiency of a heart, or the ability of the heart to pump blood out of the left ventricle and into the circulatory system of the body. EF is commonly measured as a percentage of the blood expelled from the left ventricle during the contraction phase of a heartbeat to the total capacity of the left ventricle. An EF of a normal-functioning heart may be between 50% and 70%. Preserved EF typically refers to a measure of 50% or higher. Reduced EF typically refers to a measure of 40% or lower. An EF between 40% and 50% may be considered borderline. In other examples, reduced EF can refer to a measure below 50%, and preserved EF can refer to a measure above 50%.

Reduced EF (e.g., an EF below 40%) can be indicative of certain types of heart failure (HF) or cardiomyopathy. In contrast, an EF above 75% can be indicative of certain cardiac conditions, such as hypertrophic cardiomyopathy or a reduced volume of the left ventricle. While a reduced EF can indicate one type of HF (referred to as HF with reduced EF (HFrEF) or systolic HF), nearly half of HF patients present a normal or preserved EF (referred to as HF with preserved EF (HFpEF) or diastolic HF).

The prevalence of HFpEF continues to increase in the developed world with increases in common risk factors, including: age; sex (a higher prevalence for female patients); hypertension; metabolic syndrome; renal dysfunction; and obesity. Further, HFpEF patients are not responsive to all HFrEF medications and treatments. Accordingly, there is a need to augment existing HF detection and treatment to distinguish HFpEF and HFrEF, thereby increasing the sensitivity and specificity of existing medical devices and systems, improving performance and functions of specific modern medical technologies.

SUMMARY

This document discusses, among other things, systems and methods to determine an indication of heart failure with preserved ejection fraction (HFpEF) of a subject using a determined change in cardiac acceleration information (e.g., cardiac vibration, acceleration, pressure wave, or heart sound information) of the subject at exertion relative to cardiac acceleration information of the subject at rest. The system can include a signal receiver circuit configured to receive cardiac acceleration information of a subject and exertion information of the subject, and an assessment circuit configured to determine the change in cardiac acceleration information of the subject at exertion relative to cardiac acceleration information of the subject at rest, and to determine an indication of HFpEF of the subject using the determined change in cardiac acceleration information.

In Example 1, subject matter (e.g., a medical-device system) may include a signal receiver circuit configured to receive exertion information of a subject and cardiac vibration information of the subject and an assessment circuit configured to determine a change in cardiac acceleration information of the subject at exertion relative to cardiac acceleration information of the subject at rest, and to determine an indication of heart failure with preserved ejection fraction (HFpEF) of the subject using the determined change in cardiac acceleration information.

In Example 2, the subject matter of Example 1 may optionally be configured such that the signal receiver circuit is configured to receive cardiac acceleration information indicative of third heart sound (S3) or fourth heart sound (S4) information of the subject.

In Example 3, the subject matter of any one or more of Examples 1-2 may optionally be configured such that the assessment circuit is configured to determine a period of rest of the subject using the received exertion information; determine a period of exertion of the subject using the received exertion information; determine a measure of cardiac acceleration information of the subject for the determined period of rest; and determine a measure of cardiac acceleration information of the subject for the determined period of exertion, and, to determine the change in cardiac acceleration information of the subject, the assessment circuit is configured to determine a change in the determined measures of cardiac acceleration information of the subject for the determined periods of rest and exertion.

In Example 4, the subject matter of any one or more of Examples 1-3 may optionally be configured such that the assessment circuit is configured to trend determined measures of cardiac acceleration information of the subject for determined periods of rest, to trend determined measures of cardiac acceleration information of the subject for determined periods of exertion, and to determine the change in the determined measures of cardiac acceleration information of the subject using the trends.

In Example 5, the subject matter of any one or more of Examples 1-4 may optionally be configured such that the signal receiver circuit is configured to receive posture information of the subject, and the assessment circuit is configured to determine the period of rest of the subject using the received exertion information and the received posture information and to determine the period of exertion of the subject using the received exertion information and the received posture information.

In Example 6, the subject matter of any one or more of Examples 1-5 may optionally be configured such that the assessment circuit is configured to trend determined changes in cardiac acceleration information of the subject at exertion relative to cardiac acceleration information of the subject at rest, and to determine the change in cardiac acceleration information of the subject using the trend.

In Example 7, the subject matter of any one or more of Examples 1-6 may optionally be configured such that the signal receiver circuit is configured to receive the cardiac acceleration information of the subject and the exertion information of the subject using the same acceleration sensor at different times, and the assessment circuit is configured to determine a level of exertion using acceleration information from the acceleration sensor, detect a transition from a first exertion level to a second, lower transition level, determine, following the detected transition from the first exertion level to the second exertion level, a measure of cardiac acceleration information of the subject indicative of cardiac acceleration information of the subject at the first exertion level, and determine, after a recovery period following the detected transition from the first exertion level to the second exertion level, a measure of cardiac acceleration information of the subject indicative of cardiac acceleration information of the subject at the second exertion level.

In Example 8, the subject matter of any one or more of Examples 1-7 may optionally be configured to include a posture sensor configured to sense posture information of the subject, wherein the assessment circuit is configured to detect the transition from the first exertion level to the second, lower transition level using the exertion information of the subject and the posture information of the subject.

In Example 9, the subject matter of any one or more of Examples 1-8 may optionally be configured to include the acceleration sensor configured to sense cardiac acceleration information of the subject and exertion information of the subject, wherein the signal receiver circuit is configured to receive the cardiac acceleration information of the subject and the exertion information of the subject from the acceleration sensor, and the second exertion level is rest.

In Example 10, the subject matter of any one or more of Examples 1-9 may optionally be configured to include a cardiac acceleration sensor configured to sense the cardiac acceleration information of the subject and an activity sensor configured to sense exertion information of the subject, wherein the signal receiver circuit is configured to receive the cardiac acceleration information of the subject from the cardiac acceleration sensor and the exertion information of the subject from the activity sensor.

In Example 11, the subject matter of any one or more of Examples 1-10 may optionally be configured such that the assessment circuit is configured to determine the indication of HFpEF of the subject using a determined change in cardiac acceleration information at exertion relative to cardiac acceleration information of the subject at rest greater than an HFpEF threshold.

In Example 12, the subject matter of any one or more of Examples 1-11 may optionally be configured such that, to determine the indication of HFpEF of the subject, the assessment circuit is configured to determine an indication of worsening HFpEF of the subject using the determined change in cardiac acceleration information, the example further comprising a user interface configured to provide a human-perceptible alert to the subject or a clinician using the determined indication of worsening HFpEF of the subject.

In Example 13, subject matter (e.g., a method of controlling a medical-device system) may include receiving exertion information of a subject and cardiac acceleration information of the subject using a signal receiver circuit, determining a change in cardiac acceleration information of the subject at exertion relative to cardiac acceleration information of the subject at rest using an assessment circuit, and determining an indication of heart failure with preserved ejection fraction (HFpEF) of the subject using the determined change in cardiac acceleration information.

In Example 14, the subject matter of any one or more of Examples 1-13 may optionally be configured such that determining the change in cardiac acceleration information of the subject comprises: determining a period of rest of the subject using the received exertion information; determining a period of exertion of the subject using the received exertion information; determining a measure of cardiac acceleration information of the subject for the determined period of rest; and determining a measure of cardiac acceleration information of the subject for the determined period of exertion, and determining the change in cardiac acceleration information of the subject includes determining a change in the determined measures of cardiac acceleration information of the subject for the determined periods of rest and exertion.

In Example 15, the subject matter of any one or more of Examples 1-14 may optionally be configured to include trending determined measures of cardiac acceleration information of the subject for determined periods of rest and trending determined measures of cardiac acceleration information of the subject for determined periods of exertion, wherein determining the change in the determined measures of cardiac acceleration information of the subject includes using the trends and determining the indication of HFpEF of the subject includes determining an indication of worsening HFpEF of the subject using the determined change in the determined measures of cardiac acceleration information of the subject.

In Example 16, the subject matter of any one or more of Examples 1-15 may optionally be configured to include receiving posture information of the subject using the signal receiver circuit, wherein determining the period of rest of the subject includes using the received exertion information and the received posture information and determining the period of exertion of the subject includes using the received exertion information and the received posture information.

In Example 17, the subject matter of any one or more of Examples 1-16 may optionally be configured to include trending determined changes in cardiac acceleration information of the subject at exertion relative to cardiac acceleration information of the subject at rest, wherein determining the change in cardiac acceleration information of the subject includes using the trend.

In Example 18, the subject matter of any one or more of Examples 1-17 may optionally be configured such that receiving the cardiac acceleration information of the subject and the exertion information of the subject includes using the same acceleration sensor at different times, the example further comprising: determining a level of exertion using acceleration information from the acceleration sensor; detecting a transition from a first exertion level to a second, lower transition level; determining, following the detected transition from the first exertion level to the second exertion level, a measure of cardiac acceleration information of the subject indicative of cardiac acceleration information of the subject at the first exertion level; and determining, after a recovery period following the detected transition from the first exertion level to the second exertion level, a measure of cardiac acceleration information of the subject indicative of cardiac acceleration information of the subject at the second exertion level, wherein the second exertion level is rest.

In Example 19, the subject matter of any one or more of Examples 1-18 may optionally be configured to include sensing the cardiac acceleration information of the subject using a cardiac acceleration sensor and sensing exertion information of the subject using an activity sensor, wherein receiving the cardiac acceleration information of the subject includes from the cardiac acceleration sensor and receiving the exertion information of the subject includes from the activity sensor.

In Example 20, the subject matter of any one or more of Examples 1-19 may optionally be configured such that determining the indication of HFpEF of the subject includes using a determined change in cardiac acceleration information at exertion relative to cardiac acceleration information of the subject at rest greater than an HFpEF threshold.

In Example 21, subject matter (e.g., a system or apparatus) may optionally combine any portion or combination of any portion of any one or more of Examples 1-20 to include "means for" performing any portion of any one or more of the functions or methods of Examples 1-20, or a "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Heart sounds are recurring mechanical signals associated with cardiac vibrations or accelerations from blood flow through the heart or other cardiac movements with each cardiac cycle and can be separated and classified according to activity associated with such vibrations, accelerations, movements, pressure waves, or blood flow. Heart sounds include four major features: the first through the fourth heart sounds. The first heart sound (S1) is the vibrational sound made by the heart during closure of the atrioventricular (AV) valves, the mitral valve and the tricuspid valve, at the beginning of systole. The second heart sound (S2) is the vibrational sound made by the heart during closure of the aortic and pulmonary valves at the beginning of diastole. The third and fourth heart sounds (S3, S4) are related to filling pressures of the left ventricle during diastole. Valve closures and blood movement and pressure changes in the heart can cause accelerations, vibrations, or movement of the cardiac walls that can be detected using an accelerometer or a microphone, providing an output referred to herein as cardiac acceleration information. In other examples, valve movement can be detected directly via imaging technologies such as echocardiography and magnetic resonance imaging (MRI) or by intracardiac impedance plethysmography.

Various physiologic conditions can be detected using heart sounds, including, for example, acute physiologic events, such as one or more abnormal cardiac rhythms (e.g., atrial fibrillation, atrial flutter, cardiac mechanical dyssynchrony, etc.) or chronic physiologic events (e.g., ischemia, etc.). For example, heart failure (HF) can be detected using heart sounds. In particular, HF can be monitored using the third heart sound (S3), such as disclosed in the commonly assigned Siejke et al. U.S. Pat. No. 7,115,096, titled "Third Heart Sound Activity Index for Heart Failure Monitoring," herein incorporated by reference in its entirety. A HF risk score can be determined, and worsening heart failure (WHF) detection can be adjusted using a measured physiological parameter of a sensed S3 heart sound, such as disclosed in the commonly assigned An et al. U.S. Pat. No. 9,968,266, titled "Risk Stratification Based Heart Failure Detection Algorithm," herein incorporated by reference in its entirety. A physiologic indicator, such as a HF status indication, can be determined using a trend of a determined heart sound characteristic following a transition from an elevated activity level to a less elevated activity level, such as disclosed in the commonly assigned Thakur et al. U.S. Pat. No. 9,345,410, titled "Diagnostic and Optimization using Exercise Recovery Data," herein incorporated by reference in its entirety.

The present inventors have recognized, among other things, that certain existing ambulatory medical device systems may under-detect certain HF conditions, such as HF with preserved ejection fraction (HFpEF). In addition, the present inventors have recognized that HFpEF can be detected (or distinguished between HF with reduced ejection fraction (HFrEF)) using specific cardiac acceleration (e.g., cardiac vibration, pressure waveform, endocardial acceleration, heart sound, etc.) information, such as exertional heart sounds, including particular heart sound information at a particular level of activity, such as an elevated level of activity, or heart sound information following a transition from an elevated activity level to a less elevated activity level. In an example, the heart sound information following the transition can include information directly following the transition, such that the heart sound information is indicative of that during the elevated activity level, in certain examples, taking into account the time following the detected transition, such as to account for any recovery or change in the detected heart sound information.

Certain physiologic information can be detected using heart sounds. For example, atrial filling pressure can be detected using heat sound information, such as illustrated in the commonly assigned Siejko et al. U.S. Pat. No. 7,972,275, titled "Method and Apparatus for Monitoring of Diastolic Hemodynamics", or the commonly assigned Patangay et al. U.S. Pat. No. 8,048,001, titled "Method and Apparatus for Detecting Atrial Filling Pressure", each of which are hereby incorporated by reference in their entirety.

There are fundamental differences in heart sound information between HFpEF patients and HFrEF patients. For example, a baseline S3 may be lower in HFpEF patients as compared to HFrEF patients, but may rise abnormally with exertion, indicating an exaggerated hemodynamic response. Exertion can be detected using activity or posture information. Changes in S3 with exertion, at elevated levels of activity, or following elevated levels of activity or a transition from a first level of activity to a second lower level of activity, may increase sensitivity or specificity of HFpEF detection, or enable HFpEF detection in existing systems previously not able to detect such conditions.

Increased sensitivity or specificity of detection can increase data collection and storage efficiency, providing a more robust patient monitoring system, in certain examples, using less storage or data processing than existing systems. Moreover, improved detection of conditions or detection of additional conditions in sophisticated, regulatory-compliant medical systems, components, or machinery may increase the efficiency of medical system resources, improving the functioning of modern regulated technological systems and methods not capable of being performed or managed by generic computers, components, or machinery.

Figure 1:
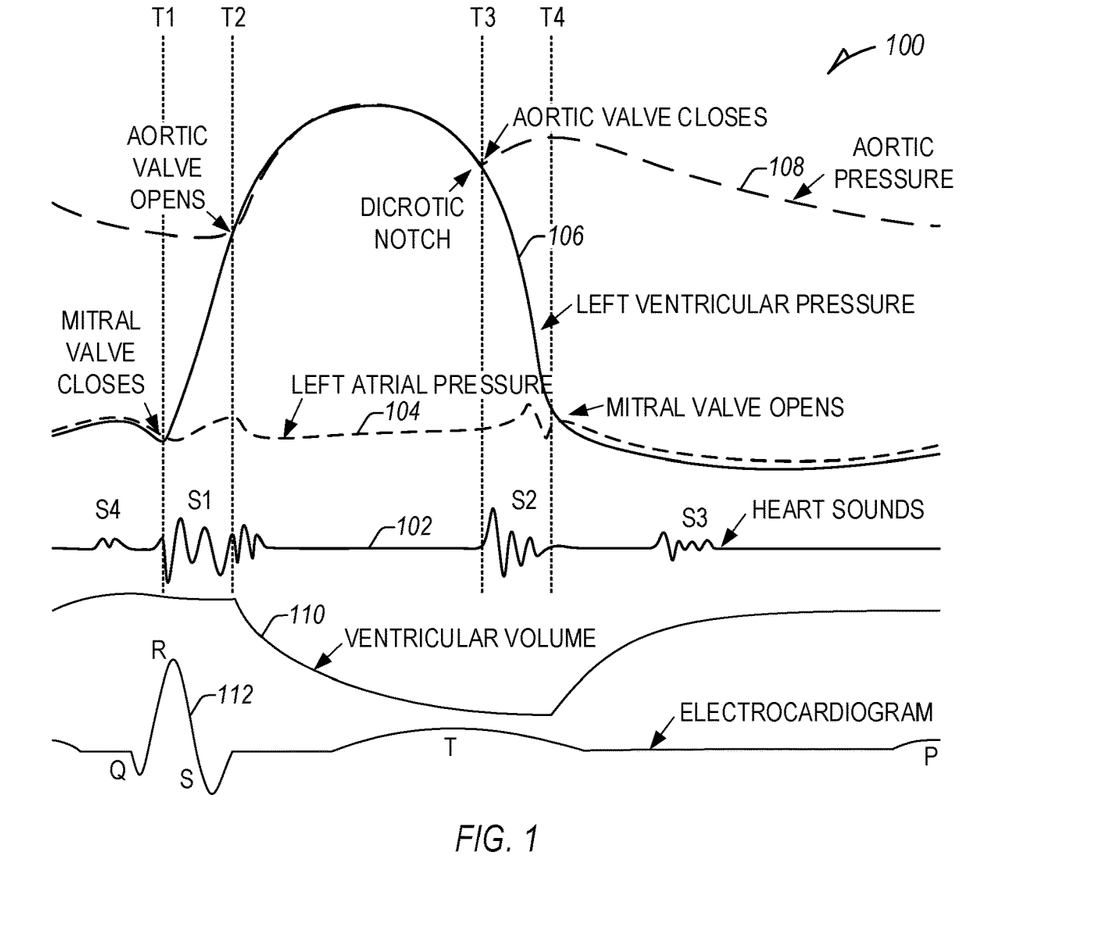
FIGS. 1-4 illustrate example relationships between physiologic information of a subject.

FIG. 1 illustrates an example relationship 100 between physiologic information, including heart sounds 102 (first, second, third, and fourth heart sounds (S1, S2, S3, and S4)), left atrial pressure 104, left ventricular pressure 106, aortic pressure 108, ventricular volume 110, and an electrocardiogram 112, such as detected from one or more sensors.

At a first time (T1), a mitral valve closes, marking a rise in left ventricular pressure 106, and the start of the first heart sound (Si) and systole, or ventricular contraction. At a second time (T2), an aortic valve opens, marking a rise in aortic pressure 108, a drop in ventricular volume 110, and continuing S1. S1 is caused by closure of the atrioventricular (AV) valves, including the mitral and tricuspid valves, and can be used to monitor heart contractility. As the left ventricular pressure 106 falls, the plethysmogram 114 rises.

At a third time (T3), an aortic valve closes, causing a dicrotic notch in the aortic pressure 108 and the second heart sound (S2), and marking the end of systole, or ventricular contraction, and the beginning of diastole, or ventricular relaxation. S2 can be used to monitor blood pressure. At a fourth time (T4), the mitral valve opens, the left atrial pressure 104 drops, and the ventricular volume 110 increases. An abrupt halt of early diastolic filling can cause the third heart sound (S3), which can be indicative of (or an early sign of) heart failure (HF). As the left ventricular pressure 106 relaxes, and the ventricular volume 110 increases, the plethysmogram 114 falls. Vibrations due to atrial kick can cause the fourth heart sound (S4), which can be used to monitor ventricular compliance.

Systolic time intervals, such as pre-ejection period (PEP) or left ventricular ejection time (LVET) can be indicative of clinically relevant information, including contractility, arrhythmia, Q-T prolongation (with electrogram (EGM) information), etc. The PEP can be measured from a Q wave of an EGM to the time of the aortic valve opening, T2 in FIG. 1. The LVET can include a time between the aortic valve opening, T2, and the aortic valve closing, T3. In other examples, one or more systolic time intervals can be detected and used to detect physiologic information of a subject (e.g., PEP/LVET, one or more mechanical, electrical, or mechanical-electrical time intervals, etc.).

Figure 2:
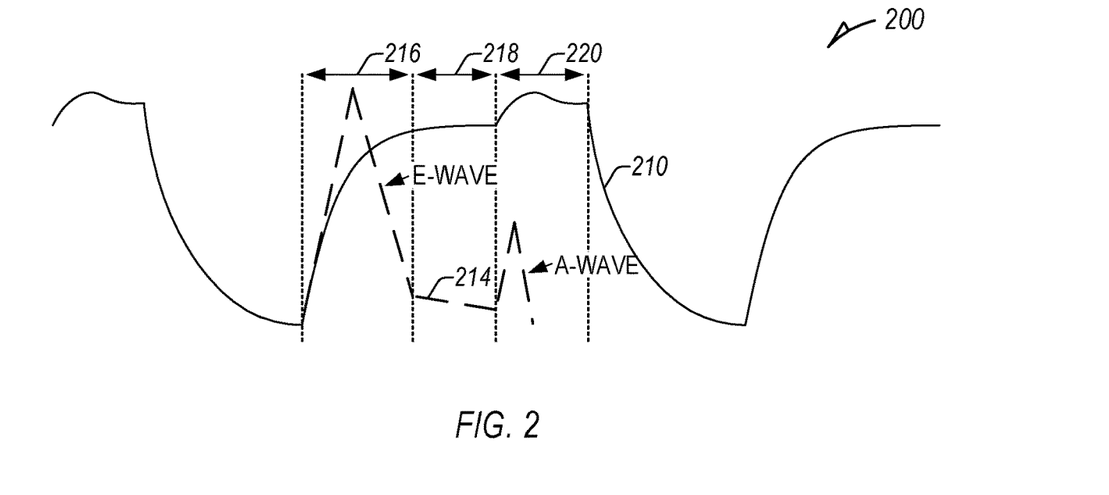

FIG. 2 illustrates an example relationship 200 between physiologic information, including ventricular volume 210 and ventricular filling velocities 214, such as detected or derived from one or more sensors (e.g., a pressure sensor, a Doppler echocardiography, ultrasound imaging, etc.) in three periods of diastole: an early filling (or rapid or passive filling) period 216; a slow filling period 218; and a late filling period 220. The ventricular filling velocities 214 have two peaks: an E-wave in the early filling period 216; and an A-wave in the late filling period 220. 70-85% of ventricular filling occurs during the early filling period 216, and 15-20% occurs during the late filling period 220.

The E-wave provides information about left atrial (LA) pressure in early diastole and occurs immediately following the isovolumetric relaxation time (IVRT) and mitral valve opening. A deceleration time (DT) of the E-wave (EDT) (or the slope or time of the second, downward edge of the E-wave in FIG. 2) is affected by the rate of rise in LV diastolic pressure (LVDP) due to early filling. Rapid cessation of flow can indicate a rapidly rising pressure in the LV or rapid emptying of the LA into a highly compliant LV. The A-wave velocity can be affected by LA pressure and LV compliance at the end of diastole. A-wave magnitude and duration can be affected by a stiffness of the ventricles. The ventricular filling velocities 214 can be characterized by the shape, timing, or magnitude of the E-wave or the A-wave, or a ratio, timing, or other measure between the E-wave and the A-wave, such as an E/A ratio (a ratio of the magnitude of the E-wave to the magnitude of the A-wave) or the EDT, and HF can be detected using one or more measures or characterizations of the ventricular filling velocities 214. Normal diagnostic function can be characterized by an E/A ratio between 0.8 and 2, declining with age.

The third heart sound (S3) is coincident with the deceleration phase of the E-wave and suggestive of a restrictive filling pattern with a steep E-wave deceleration. Detection of S3 using phonocardiography can be associated with a higher E-wave magnitude and a shorter EDT and can be correlated to the EDT (a correlation coefficient (r)=0.43). Acceleration information (e.g., HS information) indicative of the S3 can be coincident with the deceleration phase of the E-wave and can be inversely correlated to the EDT. A detected S3 (in mG) can be correlated to the EDT (r=0.55). One or more characteristics or measures of S3 (e.g., amplitude, energy, timing, etc.) can be used to determine an indication of EDT, or to detect EDT changes.

E-waves are expected to be unusually long in HFpEF. A long EDT is one diagnostic criteria for HFpEF. For example, for patients under 50 years of age, an E/A ratio less than 1.0 and an EDT greater than 220 ms is indicative of HFpEF. For patients over 50 years of age, an E/A ratio less than 0.5 and an EDT greater than 280 ms is indicative of HFpEF. From first principles, it could be expected that a longer EDT and lower E/A ratio would result in a lower (or no) S3 in HFpEF. However, the present inventors have recognized that EDT can significantly shorten during exercise. Even if S3 is too low to detect in HFpEF at rest, it can be prominent at exertion. A large portion of HFpEF patients may not show S3 or EDT abnormalities at rest, but significant exacerbations at exertion. HFpEF can be detected using an increase in an E-wave measure or the combination of increases in E-wave and S3 measures during or immediately following exertion.

Figure 3:
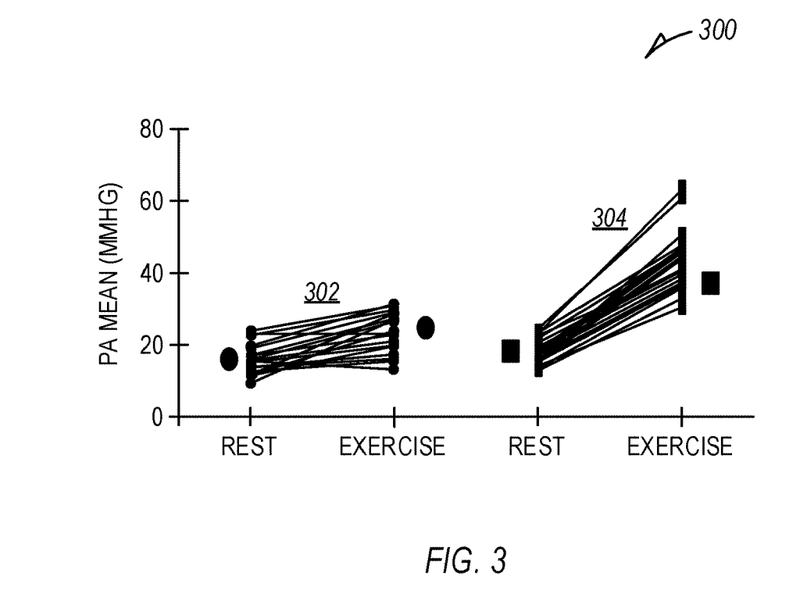
Figure 4:
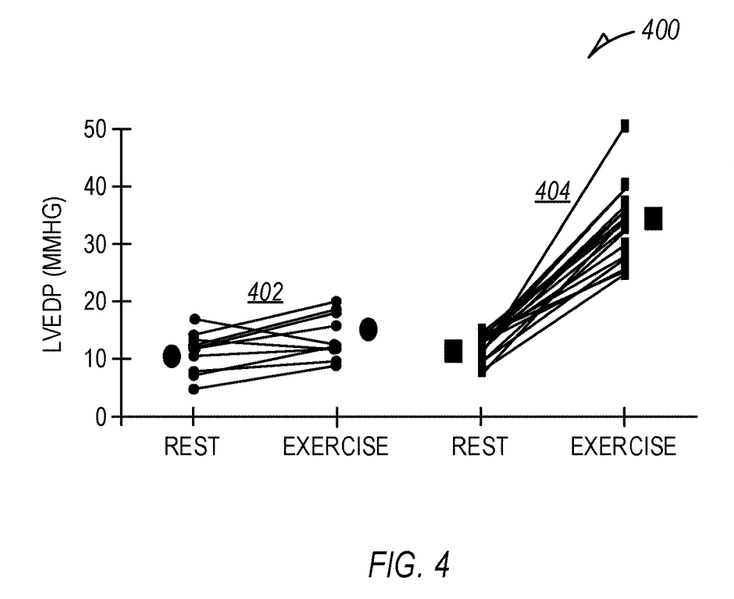

FIGS. 3 and 4 illustrate generally example physiologic information at rest and during exercise. FIG. 3 illustrates pulmonary artery (PA) mean pressure information 300 at rest and at exercise (or exertion) for patients with non-cardiac etymologies of dyspnea (NCD) 302 and for patients with HFpEF 304. For patients with NCD 302, the difference between rest and exercise is roughly 20%, whereas for patients with HFpEF 304, the difference between rest and exercise is higher, roughly 100%.

FIG. 4 illustrates LV end-diastolic pressure (LVEDP) information 400 at rest and at exercise for patients with NCD 402 and for patients with HFpEF 404. For patients with NCD 402, the difference between rest and exercise is again, roughly 20%, whereas for patients with HFpEF 404, the difference between rest and exercise is higher, greater than 100%.

Indications or measures of certain physiologic information can be determined using HS. For example, indications of or more of mean PA pressure, LVEDP, EDT, or one or more other E-wave measures (e.g., amplitude, timing, etc.) can be determine using S3 information. In certain examples, one or more E-wave measures (e.g., amplitude, timing, etc.) can be determined using S4 information. A measure, indication, or change of E/A ratio, for example, can be determined using a comparison of S3 and S4 information. Accordingly, HFpEF can be detected, or existing HF detection or existing medical device systems or methods can be confirmed, augmented, or improved using measures or changes of HS information, such as S3 or S4 information, at rest in contrast to at or following (e.g., immediately following) exercise or exertion.

Ambulatory medical devices (AMDs), including implantable or wearable medical devices, can be configured to monitor, detect, or treat various cardiac conditions associated with a reduced ability of a heart to sufficiently deliver blood to a body, such HF, arrhythmias, hypertension, etc. An AMD can include a single device or a plurality of medical devices or monitors implanted in a subject's body or otherwise positioned on or about the subject to monitor subject physiologic information of the subject, such as heart sounds, respiration (e.g., respiration rate, tidal volume, etc.), impedance (e.g., thoracic impedance, cardiac impedance, etc.), pressure (e.g., blood pressure), cardiac activity (e.g., heart rate), physical activity, posture, plethysmography, or one or more other physiologic parameters of a subject, or to provide electrical stimulation or one or more other therapies or treatments to optimize or control contractions of the heart.

In an example, the AMD can include one or more of: a respiration sensor configured to receive respiration information (e.g., a respiration rate (RR), a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); or one or more other sensors configured to receive physiologic information of the subject.

Traditional cardiac rhythm management (CRM) devices, such as pacemakers, defibrillators, or cardiac resynchronizers, include subcutaneous devices configured to be implanted in a chest of a subject, having one or more leads to position one or more electrodes or other sensors at various locations in or near the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the subject.

Implantable devices can additionally include leadless cardiac pacemakers (LCP), small (e.g., smaller than traditional implantable CRM devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Wearable or external medical sensors or devices can be configured to detect or monitor physiologic information of the subject without required implant or an in-patient procedure for placement, battery replacement, or repair. However, such sensors and devices, in contrast to implantable medical devices, may have reduced patient compliance, increased detection noise, or reduced detection sensitivity.

For each ambulatory medical device (AMD) described above (e.g., implantable medical device (IMD) or wearable medical devices (WMD)), each additional sensor can increase system cost and complexity, reduce system reliability, or increase the power consumption and reduce the usable life of the ambulatory device. Accordingly, it can be beneficial to use a single sensor to determine multiple types of physiologic information, or a smaller number of sensors to measure a larger number of different types of physiologic information.

In an example, an accelerometer, microphone, or acoustic sensor can sense or detect acceleration information of the subject including or indicative of cardiac acceleration information (e.g., heart sound information, such as from pressure waveforms due to cardiac vibrations; endocardial acceleration information, such as from acceleration information detected on or within a cardiac chamber; cardiac vibration information; etc.) of the subject. In certain examples, the same or different accelerometer, microphone, acoustic sensor or one or more other activity, posture, or exertion sensors can receive exertion information (e.g., activity information, posture information, etc.) of the subject. Exertion information can include physical activity information of the subject occurring at a different frequency than cardiac acceleration information. Accordingly, the sampling rate to detect physical activity information of the subject is often much lower than that required to detect cardiac acceleration information (e.g., exertion is often detected at a sampling rate of 50 Hz or less, whereas cardiac acceleration information is often detected at a sampling rate of 1 kHz or higher).

In an example, a single sensor can detect acceleration information at a detection period and sampling rate such that both cardiac acceleration information and exertional information can be determined from the detected acceleration information over the same or overlapping time periods. However, such determination of the separate cardiac acceleration information and the exertion information from the same acceleration information can require substantial processing time and resources. Accordingly, when a single sensor is used to detect cardiac acceleration information and exertion information, the cardiac acceleration information and the exertion information are more often detected in non-overlapping time periods (e.g., the single sensor detects one of the cardiac acceleration information or the exertional information at a time) at different sampling rates and with different pre-processing (e.g., filters, signal conditioning, etc.), such as to reduce the processing resources required to sense and process the separate information in the AMD or medical-device system having limited or different storage, processing, power, and performance capabilities.

In other examples, different sensors (or a single sensor with different physical sensing portions or components) can be used to detect the cardiac acceleration information and the exertion information. For example, it can be advantageous to detect physical activity or exertion information using a more rigid sensor tuned to sense activity having a higher magnitude and lower frequency response than cardiac acceleration information; whereas it can be advantageous to detect cardiac acceleration information using sensor having higher sensitivity and sampling frequency (e.g., a microphone instead of an accelerometer, etc.). In certain examples, separate axes of a multi-axis sensor can be used to detect different information at different sampling rates.

In certain examples, an assessment circuit can be configured to determine a change in cardiac acceleration information of the subject at exertion relative to cardiac acceleration information of the subject at rest. The assessment circuit can determine a subject status or an indication, risk, or stratification of worsening subject condition (e.g., HFpEF) using the determined change in cardiac acceleration information. The assessment circuit can provide acute or chronic monitoring of the subject condition, and can provide an alert or indication to the subject or a clinician that the subject seek medical treatment or be hospitalized in response to a determined change, or otherwise determine one or more therapy parameters, such as to be provided to a clinician for consideration, or to propose, control, or otherwise manage one or more therapies to the subject or one or more functions, modes, or operations of one or more components of a medical-device system.

Figure 5:
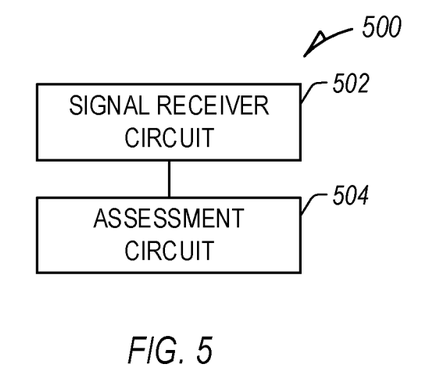
FIG. 5 illustrates an example medical-device system including a signal receiver circuit and an assessment circuit.

FIG. 5 illustrates an example system (e.g., a medical device, etc.) 500 including a signal receiver circuit 502 and an assessment circuit 504. The signal receiver circuit 502 can be configured to receive subject information, such as physiologic information of a subject, a patient (or a group of subjects or patients) from one or more sensors. The assessment circuit 504 can be configured to receive information from the signal receiver circuit 502, and to determine one or more parameters (e.g., composite physiologic parameters, stratifiers, one or more pacing parameters, etc.), such as described herein.

The assessment circuit 504 can be configured to provide an output to a user, such as to a display or one or more other user interface, the output including a score, a trend, an alert, or other indication. In other examples, the assessment circuit 504 can be configured to provide an output to another circuit, machine, or process, such as to control, adjust, or cease a therapy of a medical device, a drug delivery system, etc., or otherwise alter one or more processes or functions of a medical device system.

Figure 6:
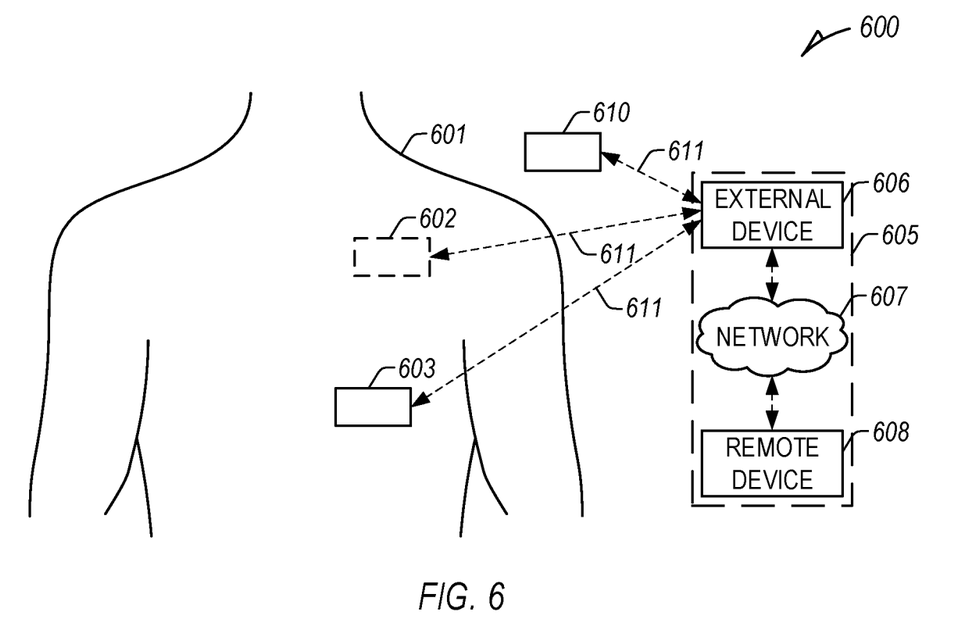
FIG. 6 illustrates an example medical-device system including an ambulatory medical device (AMD) configured to sense or detect information from a subject and an external system.

FIG. 6 illustrates an example patient management system 600 and portions of an environment in which the system 600 may operate. The patient management system 600 can perform a range of activities, including, remote patient monitoring and diagnosis of a disease condition. Such activities can be performed proximal to a patient 601, such as in a patient home or office, through a centralized server, such as in a hospital, clinic, or physician office, or through a remote workstation, such as a secure wireless mobile computing device.

The patient management system 600 can include one or more ambulatory devices, an external system 605, and a communication link 611 providing for communication between the one or more ambulatory devices and the external system 605. The one or more ambulatory devices can include an implantable medical device (IMD) 602, a wearable medical device 603, or one or more other implantable, leadless, subcutaneous, external, wearable, or ambulatory medical devices configured to monitor, sense, or detect information from, determine physiologic information about, or provide one or more therapies to treat various cardiac conditions of the patient 601, such as high blood pressure, an ability of a heart to sufficiently deliver blood to a body, including atrial fibrillation (AF), congestive heart failure (CHF), hypertension, or one or more other cardiac or non-cardiac conditions (e.g., dehydration, hemorrhage, renal dysfunction, etc.).

In an example, the IMD 602 can include one or more traditional cardiac rhythm management (CRM) devices, such as a pacemaker or defibrillator, implanted in a chest of a subject, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the subject 601. In another example, the IMD 602 can include a monitor implanted, for example, subcutaneously in the chest of subject 601.

The IMD 602 can include an assessment circuit configured to detect or determine specific physiologic information of the subject 601, or to determine one or more conditions or provide information or an alert to a user, such as the subject 601 (e.g., a patient), a clinician, or one or more other caregivers. The IMD 602 can alternatively or additionally be configured as a therapeutic device configured to treat one or more medical conditions of the subject 601. The therapy can be delivered to the subject 601 via the lead system and associated electrodes or using one or more other delivery mechanisms. The therapy can include anti-arrhythmic therapy to treat an arrhythmia or to treat or control one or more complications from arrhythmias, such as syncope, congestive heart failure (CHF), or stroke, among others. In other examples, the therapy can include delivery of one or more drugs to the subject 601 using the IMD 602 or one or more of the other ambulatory devices. Examples of the anti-arrhythmic therapy include pacing, cardioversion, defibrillation, neuromodulation, drug therapies, or biological therapies, among other types of therapies. In other examples, therapies can include cardiac resynchronization therapy (CRT) for rectifying dyssynchrony and improving cardiac function in CHF patients. In some examples, the IMD 602 can include a drug delivery system, such as a drug infusion pump to deliver drugs to the patient for managing arrhythmias or complications from arrhythmias, hypertension, or one or more other physiologic conditions. In yet other examples, the IMD 602 can include a therapy circuit or module configured to treat hypertension (e.g., a neurostimulation therapy circuit, a drug delivery therapy circuit, a stimulation therapy circuit, etc.).

The wearable medical device 603 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.). The wearable medical device 603 can include an optical sensor configured to detect a photoplethysmogram (PPG) signal on a wrist, finger, or other location on the subject 601. In other examples, the wearable medical device 603 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The patient management system 600 can include, among other things, a respiration sensor configured to receive respiration information (e.g., a respiration rate (RR), a respiration volume (tidal volume), etc.), a heart sound sensor configured to receive heart sound information, a thoracic impedance sensor configured to receive impedance information, a cardiac sensor configured to receive cardiac electrical information, an activity sensor configured to receive information about a physical motion (e.g., activity, posture, etc.), a plethysmography sensor, or one or more other sensors configured to receive physiologic information of the subject 601.

The external system 605 can include a dedicated hardware/software system, such as a programmer, a remote server-based patient management system, or alternatively a system defined predominantly by software running on a standard personal computer. The external system 605 can manage the subject 601 through the IMD 602 or one or more other ambulatory devices connected to the external system 605 via a communication link 611. In other examples, the IMD 602 can be connected to the wearable device 603, or the wearable device 603 can be connected to the external system 605, via the communication link 611. This can include, for example, programming the IMD 602 to perform one or more of acquiring physiological data, performing at least one self-diagnostic test (such as for a device operational status), analyzing the physiological data to detect a cardiac arrhythmia, or optionally delivering or adjusting a therapy to the subject 601. Additionally, the external system 605 can send information to, or receive information from, the IMD 602 or the wearable device 603 via the communication link 611. Examples of the information can include real-time or stored physiological data from the subject 601, diagnostic data, such as detection of cardiac arrhythmias or events of worsening heart failure, responses to therapies delivered to the subject 601, or device operational status of the IMD 602 or the wearable device 603 (e.g., battery status, lead impedance, etc.). The communication link 611 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 605 can include an external device 606 in proximity of the one or more ambulatory devices, and a remote device 608 in a location relatively distant from the one or more ambulatory devices, in communication with the external device 606 via a communication network 607. Examples of the external device 606 can include a medical device programmer.

The remote device 608 can be configured to evaluate collected subject or patient information and provide alert notifications, among other possible functions. In an example, the remote device 608 can include a centralized server acting as a central hub for collected data storage and analysis. The server can be configured as a uni-, multi-, or distributed computing and processing system. The remote device 608 can receive data from multiple subjects or patients. The data can be collected by the one or more ambulatory devices, among other data acquisition sensors or devices associated with the subject 601. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory devices, such as the IMD. By way of example, alert notifications can include a Web page update, phone or pager call, E-mail, SMS, text or "Instant" message, as well as a message to the subject or patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiological data associated with the detected medical event to physiological data associated with the historical alerts.

The remote device 608 may additionally include one or more locally configured clients or remote clients securely connected over the communication network 607 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 608, including the server and the interconnected clients, may also execute a follow-up scheme by sending follow-up requests to the one or more ambulatory devices, or by sending a message or other communication to the subject 601 (e.g., the patient), clinician or authorized third party as a compliance notification.

The communication network 607 can provide wired or wireless interconnectivity. In an example, the communication network 607 can be based on the Transmission Control Protocol/Internet Protocol (TCP/IP) network communication specification, although other types or combinations of networking implementations are possible. Similarly, other network topologies and arrangements are possible.

One or more of the external device 606 or the remote device 608 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 606 or the remote device 608 can include a respective display unit for displaying the physiological or functional signals, or alerts, alarms, emergency calls, or other forms of warnings to signal the detection of arrhythmias. In some examples, the external system 605 can include an external data processor configured to analyze the physiological or functional signals received by the one or more ambulatory devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory devices or the external system 605 can be implemented using hardware, software, firmware, or combinations thereof. Portions of the one or more ambulatory devices or the external system 605 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The patient management system 600 can include a therapy device, such as a drug delivery device configured to provide therapy or therapy information (e.g., dosage information, etc.) to the subject 601, such as using information from one or more of the ambulatory devices. In other examples, one or more of the ambulatory devices can be configured to provide therapy or therapy information to the subject 601. The therapy device can be configured to send information to or receive information from one or more of the ambulatory devices or the external system 605 using the communication link 611. In an example, the one or more ambulatory devices, the external device 606, or the remote device 608 can be configured to control one or more parameters of the therapy device 610.

The patient management system 600 can include a patient chronic condition-based HF assessment circuit, such as illustrated in the commonly assigned Qi An et al., U.S. application Ser. No. 14/510,392, incorporated herein by reference in its entirety. The patient chronic condition-based HF assessment circuit can include a signal analyzer circuit and a risk stratification circuit. The signal analyzer circuit can receive patient chronic condition indicators and one or more physiologic signals from a patient and select one or more patient-specific sensor signals or signal metrics from the physiologic signals. The signal analyzer circuit can receive the physiologic signals from the patient using the electrodes on one or more of the leads, or physiologic sensors deployed on or within the patient and communicated with one or more other components of the patient management system 600. The risk stratification circuit can generate a composite risk index indicative of the probability of the patient later developing an event of worsening of HF (e.g., an HF decompensation event) such as using the selected patient-specific sensor signals or signal metrics. The HF decompensation event can include one or more early precursors of an HF decompensation episode, or an event indicative of HF progression such as recovery or worsening of HF status.

The external system 605 can allow for programming the one or more ambulatory devices and can receives information about one or more signals acquired by the one or more ambulatory devices, such as can be received via a communication link 611. The external system 605 can include a local external IMD programmer. The external system 605 can include a remote patient management system that can monitor patient status or adjust one or more therapies such as from a remote location.

The patient chronic condition-based HF assessment circuit, or other assessment circuit, may be implemented at the external system 605, which can be configured to perform HF risk stratification such as using data extracted from the one or more ambulatory devices or data stored in a memory within the external system 605. Portions of patient chronic condition-based HF or other assessment circuit may be distributed between the one or more ambulatory devices and the external system 605.

Figure 7:
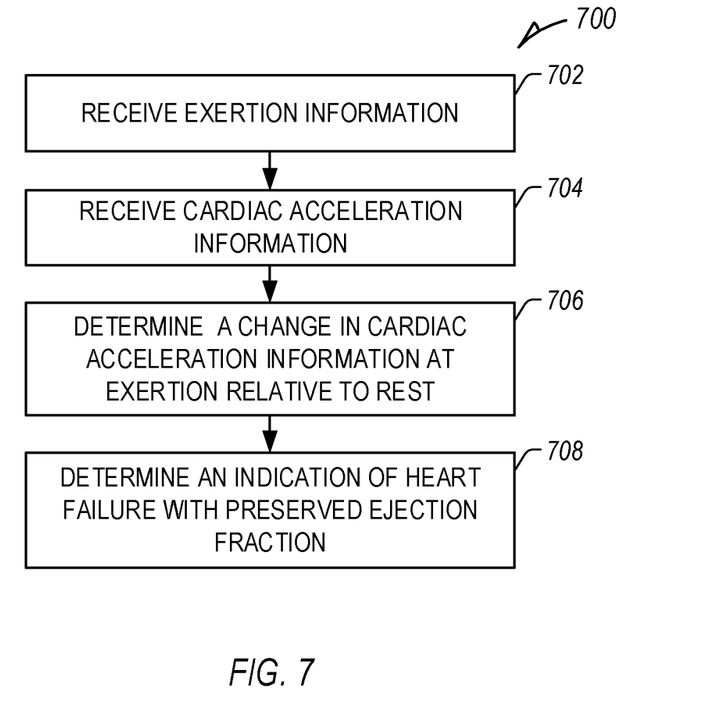
FIG. 7 illustrates an example method including determining an indication of heart failure with preserved ejection fraction (HFpEF) of a subject using a determined change in cardiac acceleration information of the subject.

FIG. 7 illustrates an example method 700 of controlling or otherwise altering a function of a medical-device system. At 702, exertion information is received, such as by the signal receiver circuit from an exertion sensor. Exertion information can include acceleration information indicative of activity of a subject. An assessment circuit can be configured to determine a period of rest of the subject or a period of exertion of the subject using the received exertion information. The period of exertion of the subject can include activity information of the subject at or above a threshold, or an amount of aggregate activity of the subject over a given period of time. The period of rest of the subject can include activity information of the subject below a threshold.

In an example, the exertion sensor can include a posture sensor, or the signal receiver can be configured to receive information from a posture sensor. A detected change in posture can be used, in certain examples, in combination with exertion or activity information, to determine periods of rest or exertion. For example, if the posture or activity information indicates that the subject is sitting or laying down, or is inactive, a detected period of activity is unlikely without a change in posture. Accordingly, a change in posture can be used, in part, to define a transition between activity levels, such as a transition from a period of exertion, or activity above a threshold, to a period of rest.

At 704, cardiac acceleration information (e.g., heart sound information) is received, such as by a signal receiver circuit from an acceleration sensor (e.g., an accelerometer, a microphone, etc.), such as during determined periods of rest or exertion. The cardiac acceleration information can include one or more heart sounds of the subject, such as one or more of a first, second, third, or fourth heart sound (S1-S4), and the acceleration sensor can include a heart sound sensor, such as a microphone or an accelerometer. In an example, cardiac acceleration information can be received regularly and stored according to exertion information, such as an activity level, or a determined period of exertion or rest. In other examples, exertion information can be determined, and cardiac acceleration information can be received for specific desired periods of exertion or rest or levels of activity. For a determined period of rest, cardiac acceleration information can be received, stored, or measured after a transition from exertion to rest and a waiting time long enough for the patient physiologic information to reach a resting baseline (e.g., several minutes following a transition, or longer). However, for the determined period of activity, cardiac acceleration information can be received, stored, or measured immediately following a detected transition from exertion to rest, such as to detect physiologic information indicative of peak physical exertion, or to detect cardiac acceleration information as close to peak exertion as possible in situations where a single sensor is used to determine exertion and cardiac acceleration information. In certain examples, during sustained periods of exertion, an acceleration sensor can transition from detecting exertion information to detecting cardiac acceleration information before transitioning back to detecting exertion information.

At 706, a change in cardiac acceleration information at exertion relative to rest is determined, such as by the assessment circuit. The assessment circuit can be configured to determine a measure of cardiac acceleration information of the subject for the determined period of rest and to determine a measure of cardiac acceleration information of the subject for the determined period of exertion. To determine the change in cardiac acceleration information of the subject, the assessment circuit can be configured to determine a change in the determined measures of cardiac acceleration information of the subject for the determined periods of rest and exertion. In certain examples, the assessment circuit can determine short-term, long-term, or daily values (e.g., averages, maximums, minimums, counts in certain percentiles, etc.) of cardiac acceleration information at rest and at exertion. In other examples, the assessment circuit can trend the measures of cardiac acceleration information at rest and at exertion, or trend differences of pairs of measures of cardiac acceleration information at rest and at exertion.

In an example, a measure of cardiac acceleration information (e.g., S3 magnitude or energy in an S3 window, etc.) can be trended at one or more exertion levels, such as at or above one or more activity levels. The measure of cardiac acceleration at exertion can be compared to a measure of cardiac acceleration information at rest, or at or below one or more activity levels.

In certain examples, a transition between activity levels, such as from exertion and rest or vice versa, can be detected. Following (e.g., immediately following) the transition from exertion to rest, a measure of cardiac acceleration information can be determined and logged to the activity level prior to the transition. Measures of cardiac acceleration information can be logged or recorded at various activity levels throughout the day to create daily trends of measures of cardiac acceleration information at particular activity levels. In an example, the measures of cardiac acceleration information can be adjusted by a coefficient, such as the activity level (e.g., peak exercise intensity (E), etc.), the time (T) between the activity level and received cardiac acceleration information (e.g., 1 minute, 2 minutes, 5 minutes, etc.), or a ratio of time and activity level (e.g., T/E, etc.) The measures of cardiac acceleration information can include one or more of a magnitude, timing, or energy of S1-S4 or a ratio of such (e.g., S1/S3, S3/S4, etc.).

At 708, an indication of HFpEF is determined, such as by the assessment circuit, using the determined change in cardiac acceleration information at exertion relative to rest, such as by comparing the determined change or a trend of the determined change to a threshold (e.g., an HFpEF threshold). In certain examples, the indication of HFpEF can be used to provide a human-perceptible alert or to control or adjust a function of one or more components of a medical-device system.

Figure 8:
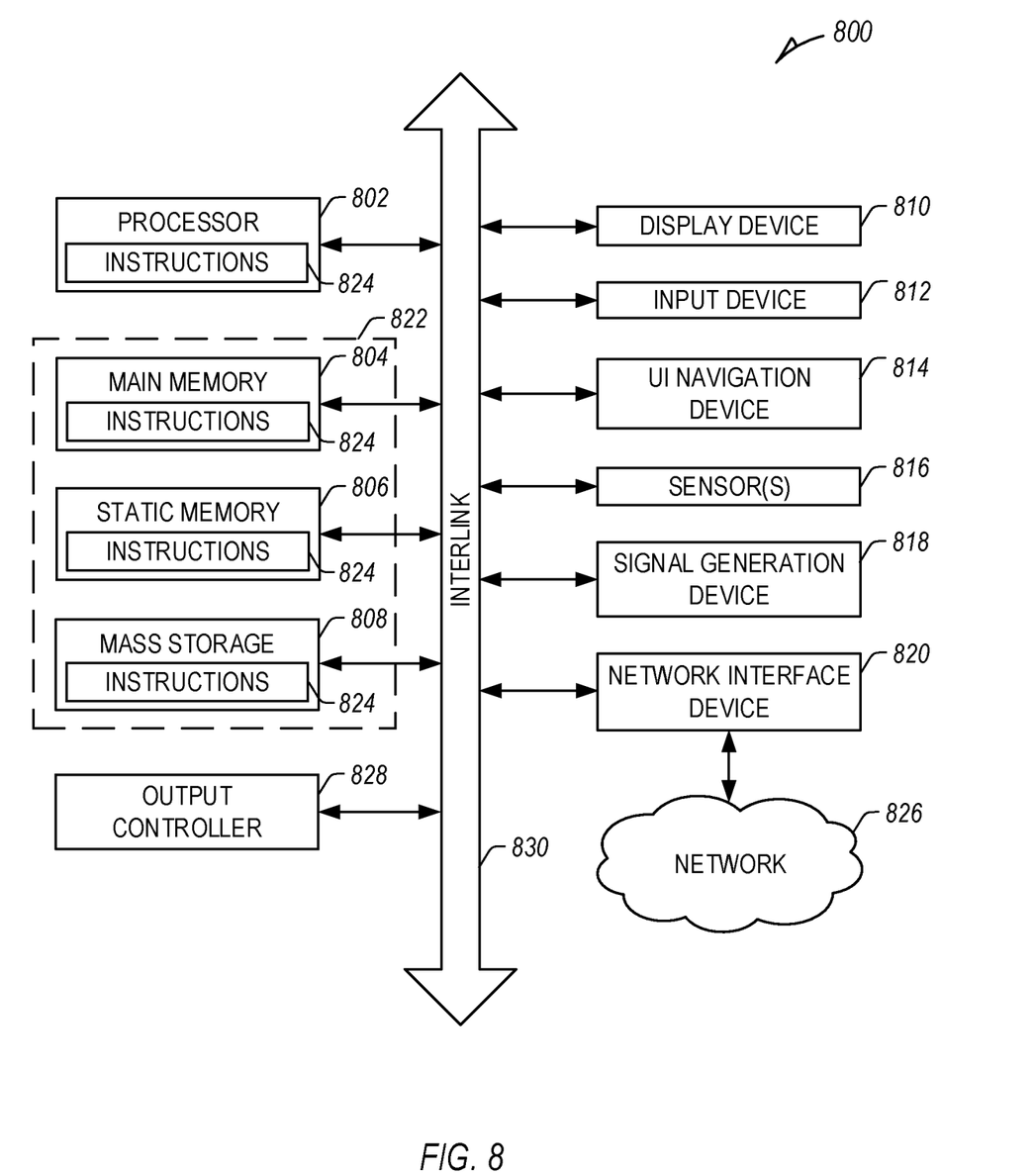
FIG. 8 illustrates a block diagram of an example machine upon which any one or more of the techniques discussed herein may perform.

FIG. 8 illustrates a block diagram of an example machine 800 upon which any one or more of the techniques (e.g., methodologies) discussed herein may perform. Portions of this description may apply to the computing framework of one or more of the medical devices described herein, such as the IMD, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 800. Circuitry (e.g., processing circuitry) is a collection of circuits implemented in tangible entities of the machine 800 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 800 follow.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 800 may include a hardware processor 802 (e.g., a central processing unit (CPU), a graphics processing unit (GPU), a hardware processor core, or any combination thereof), a main memory 804, a static memory (e.g., memory or storage for firmware, microcode, a basic-input-output (BIOS), unified extensible firmware interface (UEFI), etc.) 806, and mass storage 808 (e.g., hard drive, tape drive, flash storage, or other block devices) some or all of which may communicate with each other via an interlink (e.g., bus) 830. The machine 800 may further include a display unit 810, an alphanumeric input device 812 (e.g., a keyboard), and a user interface (UI) navigation device 814 (e.g., a mouse). In an example, the display unit 810, input device 812, and UI navigation device 814 may be a touch screen display. The machine 800 may additionally include a signal generation device 818 (e.g., a speaker), a network interface device 820, and one or more sensors 816, such as a global positioning system (GPS) sensor, compass, accelerometer, or one or more other sensors. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 802, the main memory 804, the static memory 806, or the mass storage 808 may be, or include, a machine-readable medium 822 on which is stored one or more sets of data structures or instructions 824 (e.g., software) embodying or utilized by any one or more of the techniques or functions described herein. The instructions 824 may also reside, completely or at least partially, within any of registers of the processor 802, the main memory 804, the static memory 806, or the mass storage 808 during execution thereof by the machine 800. In an example, one or any combination of the hardware processor 802, the main memory 804, the static memory 806, or the mass storage 808 may constitute the machine-readable medium 822. While the machine-readable medium 822 is illustrated as a single medium, the term "machine-readable medium" may include a single medium or multiple media (e.g., a centralized or distributed database, and/or associated caches and servers) configured to store the one or more instructions 824.

The term "machine-readable medium" may include any medium that is capable of storing, encoding, or carrying instructions for execution by the machine 800 and that cause the machine 800 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may be further transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 800, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical-device system, comprising:
   a signal receiver circuit configured to receive exertion information of a subject and cardiac vibration acceleration information of the subject, the cardiac acceleration information comprising third heart sound (S3) information of the subject; and
   an assessment circuit configured to:
     determine a period of rest of the subject using the received exertion information;
     determine a period of exertion of the subject using the received exertion information;
     determine a measure of cardiac acceleration information of the subject for the determined periods of rest;
     determine a measure of cardiac acceleration information of the subject for the determined periods of exertion;
     determine a change in magnitude or energy of the determined measure of cardiac acceleration information of the subject for the determined period of exertion relative to the determined measure of cardiac acceleration information of the subject at rest, and to for the determined period of rest;
    determine an indication of heart failure with preserved ejection fraction (HFpEF) of the subject using the determined change in magnitude or energy of the determined measures; and
    provide an output of the determined indication of HFpEF to a user interface for display to a user, or to another circuit to control or adjust a process or function of the medical-device system.

2. The system of claim 1, wherein the cardiac acceleration information comprises the S3 information of the subject and at least one of first heart sound (S1) information of the subject, second heart sound (S2) information of the subject, or fourth heart sound (S4) information of the subject, and
    wherein the measure of cardiac acceleration information comprises a ratio of the S3 information and at least one of the S1 information, the S2 information, or the S4 information.

3. The system of claim 2, wherein the S1 information, the S2 information, the S3 information, and the S4 information comprise a magnitude or energy of the respective information.

4. The system of claim 1, wherein the assessment circuit is configured to:
    trend determined measures of cardiac acceleration information of the subject for determined periods of rest;
    trend determined measures of cardiac acceleration information of the subject for determined periods of exertion; and
    determine the change in magnitude or energy of the determined measure of cardiac acceleration information of the subject for the determined period of exertion relative to the determined measure of cardiac acceleration information of the subject for the determined period of rest using the trends.

5. The system of claim 3, wherein the signal receiver circuit is further configured to receive posture information of the subject, and
    wherein the assessment circuit is configured to:
        determine the period of rest of the subject using the received exertion information and the received posture information; and
        determine the period of exertion of the subject using the received exertion information and the received posture information.

6. The system of claim 1, wherein the assessment circuit is configured to:
    trend determined changes in the determined measure of cardiac acceleration information of the subject for the determined period of exertion relative to the determined measure of cardiac acceleration information of the subject for the determined period of rest; and
    determine the change in cardiac acceleration information of the subject using the trend.

7. The system of claim 1, wherein the signal receiver circuit is configured to receive the cardiac acceleration information of the subject and the exertion information of the subject using the same acceleration sensor at different times, and
    wherein the assessment circuit is configured to:
        determine a level of exertion using acceleration information from the acceleration sensor;
        detect a transition from a first exertion level to a second, lower exertion level;
        determine, following the detected transition from the first exertion level to the second exertion level, a measure of cardiac acceleration information of the subject indicative of cardiac acceleration information of the subject at the first exertion level; and
        determine, after a recovery period following the detected transition from the first exertion level to the second exertion level, a measure of cardiac acceleration information of the subject indicative of cardiac acceleration information of the subject at the second exertion level.

8. The system of claim 7, comprising a posture sensor configured to sense posture information of the subject,
    wherein the assessment circuit is configured to detect the transition from the first exertion level to the second, lower exertion level using the exertion information of the subject and the posture information of the subject.

9. The system of claim 7, comprising the acceleration sensor configured to sense cardiac acceleration information of the subject and exertion information of the subject,
    wherein the signal receiver circuit is configured to receive the cardiac acceleration information of the subject and the exertion information of the subject from the acceleration sensor, and
    wherein the second exertion level is rest.

10. The system of claim 1, comprising:
    a cardiac acceleration sensor configured to sense the cardiac acceleration information of the subject; and
    an activity sensor configured to sense exertion information of the subject,
    wherein the signal receiver circuit is configured to receive the cardiac acceleration information of the subject from the cardiac acceleration sensor and the exertion information of the subject from the activity sensor.

11. The system of claim 1, wherein the assessment circuit is configured to determine the indication of HFpEF of the subject using a determined change in cardiac acceleration information at exertion relative to cardiac acceleration information of the subject at rest greater than an HFpEF threshold.

12. The system of claim 1, wherein, to determine the indication of HFpEF of the subject, the assessment circuit is configured to determine an indication of worsening HFpEF of the subject using the determined change in cardiac acceleration information, the system further comprising:
    a user interface configured to provide a human-perceptible alert to the subject or a clinician using the determined indication of worsening HFpEF of the subject.

13. The system of claim 1, wherein the assessment circuit is configured to distinguish between heart failure with reduced ejection fraction (HFrEF) and HFpEF using the determined change in magnitude or energy of the determined measures.

14. A method of controlling a medical-device system, comprising:
    receiving exertion information of a subject and cardiac acceleration information of the subject using a signal receiver circuit, the cardiac acceleration information comprising third heart sound (S3) information of the subject;
    determining, using an assessment circuit, a period of rest of the subject using the received exertion information;
    determining, using the assessment circuit, a period of exertion of the subject using the received exertion information;

determining, using the assessment circuit, a measure of cardiac acceleration information of the subject for the determined periods of rest;

determining, using the assessment circuit, a measure of cardiac acceleration information of the subject for the determined periods of exertion;

determining, using the assessment circuit, a change in magnitude or energy of the determined measure of cardiac acceleration information of the subject for the determined period of exertion relative to the determined measure of cardiac acceleration information of the subject for the determined period of rest;

determining, using the assessment circuit, an indication of heart failure with preserved ejection fraction (HFpEF) of the subject using the determined change in magnitude or energy of the determined measures; and providing, using the assessment circuit, an output of the determined indication of HFpEF to a user interface for display to a user, or to another circuit to control or adjust a process or function of the medical-device system.

15. The method of claim 14, wherein the cardiac acceleration information comprises the S3 information of the subject and at least one of first heart sound (S1) information of the subject, second heart sound (S2) information of the subject, or fourth heart sound (S4) information of the subject.

16. The method of claim 15, comprising:

trending determined measures of cardiac acceleration information of the subject for determined periods of rest; and trending determined measures of cardiac acceleration information of the subject for determined periods of exertion, wherein determining the change in magnitude or energy of the determined measures of cardiac acceleration information of the subject for the determined period of exertion relative to the determined period of rest includes using the trends, and wherein determining the indication of HFpEF of the subject includes using the determined change in magnitude or energy of the determined measures.

17. The method of claim 15, comprising receiving posture information of the subject using the signal receiver circuit, wherein determining the period of rest of the subject includes using the received exertion information and the received posture information, and wherein determining the period of exertion of the subject includes using the received exertion information and the received posture information.

18. The method of claim 14, comprising trending determined changes in-the determined measure of cardiac acceleration information of the subject for the determined period of exertion relative to the determined measure of cardiac acceleration information of the subject for the determined period of rest, wherein determining the change in cardiac acceleration information of the subject includes using the trend.

19. The method of claim 14, wherein receiving the cardiac acceleration information of the subject and the exertion information of the subject includes using the same acceleration sensor at different times, the method further comprising:

determining a level of exertion using acceleration information from the acceleration sensor;

detecting a transition from a first exertion level to a second, lower exertion level;

determining, following the detected transition from the first exertion level to the second exertion level, a first measure of cardiac acceleration information of the subject indicative of cardiac acceleration information of the subject at the first exertion level; and determining, after a recovery period following the detected transition from the first exertion level to the second exertion level, a second measure of cardiac acceleration information of the subject indicative of cardiac acceleration information of the subject at the second exertion level.

20. The method of claim 14, wherein determining the indication of HFpEF of the subject includes using a determined change in cardiac acceleration information at exertion relative to cardiac acceleration information of the subject at rest greater than an HFpEF threshold.

* * * * *